United States Patent [19]

Chandraratna

[11] Patent Number: 4,992,468
[45] Date of Patent: Feb. 12, 1991

[54] PHENYLETHENYL COMPOUNDS HAVING RETINOID-LIKE ACTIVITY

[75] Inventor: Roshantha A. S. Chandraratna, El Toro, Calif.

[73] Assignee: Allergan, Inc., Irvine, Calif.

[21] Appl. No.: 385,626

[22] Filed: Jul. 26, 1989

[51] Int. Cl.$^5$ .................. A61K 31/215; A61K 31/19; C07C 321/28

[52] U.S. Cl. .................. 514/532; 514/543; 514/544; 514/568; 514/570; 560/9; 560/18; 560/55; 560/65; 562/431; 562/432; 562/474; 564/162; 564/171

[58] Field of Search .......... 560/55, 65, 9, 18; 562/473, 431, 432, 474; 514/532, 543, 544, 568, 570; 564/162, 171

[56] References Cited

U.S. PATENT DOCUMENTS

| | | | |
|---|---|---|---|
| 4,326,055 | 4/1982 | Loeliger | 562/473 |
| 4,723,028 | 2/1988 | Shudo | 560/8 |
| 4,739,098 | 4/1988 | Chandraratna | 560/8 |
| 4,740,519 | 4/1988 | Shroot et al. | 514/443 |
| 4,810,804 | 3/1989 | Chandraratna | 514/311 |

FOREIGN PATENT DOCUMENTS 0130795 1/1985 European Pat. Off. .
0176034 4/1986 European Pat. Off. .

OTHER PUBLICATIONS

Mervic et al., *J. Org. Chem.*, 45, pp. 4720–4725, (1980).

*Primary Examiner*—Werren B. Lone
*Assistant Examiner*—Vera C. Clarke
*Attorney, Agent, or Firm*—Gabor L. Szekeres; Martin A. Voet; Howard J. Klein

[57] ABSTRACT

Compounds of the following formula, useful for treating diseases affected by retinoids, are disclosed herein.

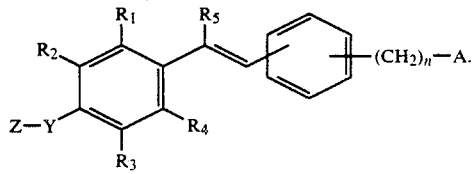

22 Claims, No Drawings

PHENYLETHENYL COMPOUNDS HAVING RETINOID-LIKE ACTIVITY

This invention relates to novel compounds having retinoid-like activity, pharmaceutical compositions comprising those compounds and the methods of using them.

SUMMARY OF THE INVENTION

The compounds of this invention are represented by the following formula:

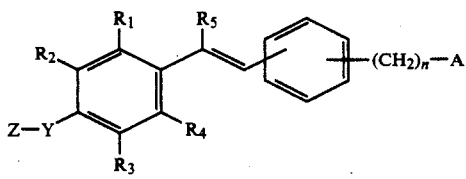

in which:
$R_1$, $R_2$, $R_3$ and $R_4$ are hydrogen, lower alkyl, halogen or lower alkoxy;
$R_5$ is hydrogen or lower alkyl;
Y is oxygen or sulfur;
Z is 1-10 carbon straight or branched alkyl or 2-10 carbon straight or branched unsaturated alkyl;
n is 0—5; and
A is H, —COOH or a pharmaceutically acceptable salt, ester or amide thereof, —CH$_2$OH or an ether or ester derivative, or —CHO or an acetal derivative, or —COR$_6$ or a ketal derivative where R$_6$ is —(CH$_2$)$_m$ CH$_3$ where m is 0—4.

This invention also relates to a pharmaceutical composition comprising a compound of formula I in admixture with a pharmaceutically acceptable excipient.

In addition, this invention relates to the use of the compounds of formula I for treating dermatoses, such as acne, Darier's disease, psoriasis, icthyosis, eczema, atopic dermatitis and epithelial cancers. These compounds are also useful in the treatment of arthritic diseases and other immunological disorders (e.g., lupus erythematosus), in promoting wound healing and in treating the dry eye syndrome, and in preventing or reversing the effects of sun damage to skin.

In another aspect, this invention relates to the process for making a compound of formula I, which process comprises reacting a compound of formula II with a compound of formula III in the presence of sodium hydride

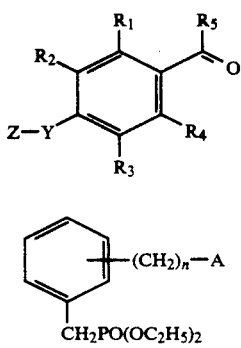

wherein $R_1$, $R_2$, $R_3$, $R_4$, $R_5$, Y and Z are as defined hereabove; converting the ester of formula I to an acid; and to prepare compounds in which n is 1—5, homologating a compound of the formula

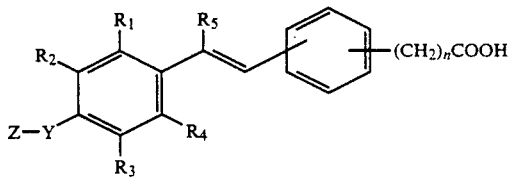

where n is 0—4, or
converting an acid of formula I to an ester; or
converting an acid of formula I to an amide; or
reducing an acid of formula I to an alcohol of aldehyde; or
converting an alcohol of formula I to an ether or ester; or
oxidizing an alcohol of formula I to an aldehyde; or
converting an aldehyde of formula I to an acetal.

GENERAL EMBODIMENTS

Definitions

The term "ester" as used here refers to and covers any compound falling within the definition of that term as classically used in organic chemistry. It includes organic and inorganic esters. Where A is —COOH, this term covers the products derived from treatment of this function with alcohols or thioalcohols. Where the ester is derived from compounds where A is —CH$_2$OH, this term covers compounds derived from organic acids capable of forming esters including phosphorous-based and sulfur-based acids, or compounds of the formula —CH$_2$OCOR where R is any substituted or unsubstituted aliphatic, aromatic, heteroaromatic or aliphatic-aromatic group.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Here, and wherever else used, lower alkyl means having 1-6 carbon atoms. Also preferred are the phenyl or lower alkyphenyl esters. Thus general formulae for the esters of the invention, with respect to the ester portion, are —CH$_2$OCOR$_7$ and COOR$_7$, where R$_7$ is alkyl, aryl or arylalkyl group.

The term "lower alkyl" means an alkyl radical of 1 to 6 carbon atoms.

Amides has the meaning classically accorded that term in organic chemistry. In this instance it includes the unsubstituted amides and all aliphatic and aromatic mono- and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and di-substituted amides derived from the substituted and unsubstituted phenyl or lower alkylphenyl amines. Unsubstituted amides are also preferred. Thus general formulae for the amides of the invention, with respect to the amide portion, are CONH$_2$, CONHR$_7$, and CON(R$_7$)$_2$, wherein R$_7$ is alkyl, aryl or arylalkyl group.

Acetals includes the radicals of the formula —CK where K is $(OR_8)_2$. Here, $R_8$ is lower alkyl. Also, K may be —$OR_9O$— where $R_9$ is lower alkyl of 2–5 carbon atoms, straight chain or branched. By analogy to the acetals, ketones and ketals within the scope of the invention may be characterized, as far as the ketone and ketal functions are concerned, by the general formula —$COR_6$ for the ketones, and by the general formulae $CR_6(OR_8)_2$ and $CR_6OR_9O$ for the ketals, where $R_6$ is —$(CH_2)_mCH_3$ where m is 0–4, $R_8$ is lower alkyl, and $R_9$ is divalent alkyl radical of 2 to 5 carbons.

A pharmaceutically acceptable salt may be prepared for any compounds in this invention having a functionality capable of forming such salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

The preferred compounds of this invention are those of formula I where the $(CH_2)_n$—A substituent is para to the ethenyl chain on the benzene ring; n is 0, 1 or 2; and A is —COOH, an alkali metal salt or organic amine salt, or a lower alkyl ester, or —$CH_2OH$ and the lower alkyl esters thereof. Particularly preferred compounds are:

ethyl 4-[E-2-methyl-2-(4-(3-methyl-2-butenoxy)-phenyl)ethenyl]benzoate;

ethyl 4-[E-2-(4-3-methyl-2-thiobutenyl)phenyl)ethenyl]benzoate.

4-[E-2-methyl-2(4-(3-methyl-2-butenoxy)phenyl)ethenyl]benzoic acid, and

4-[E-2-(4-(3-methyl-2-thiobutenyl)phenyl)ethenyl]-benzoic acid.

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, *Remington's Pharmaceutical Science*, Edition 17, Mack Publishing Company, Easton, Pa. For topical application, these compounds could also be administered as a powder or spray, particularly in aerosol form. If the drug is to be administered systemically, it may be confected as a powder, pill, tablet or the like, or as a syrup or elixir suitable for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in a prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many diseases for which these compounds are useful.

The retinoic acid-like activity of these compounds is confirmed through the classic measure of retinoic acid activity involving the effects of retinoic acid on ornithine decarboxylase. The original work on the correlation between retinoic acid and decrease in cell proliferation was done by Verma & Boutwell, *Cancer Research*, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in *Cancer Res.*: 1662–1670, 1975 may be used to demonstrate inhibition of TPA induction of ODC by compounds of this invention.

PREPARATION OF COMPOUNDS

It is anticipated that the compounds of this invention can be made by a number of different synthetic chemical pathways. To illustrate this invention, there is here laid out a series of steps which will provide the compounds of formula I when such synthesis is followed in tone and in spirit. The synthetic chemist will readily appreciate that the conditions set out here are specific embodiments which can be generalized to any and all of the compounds represented by formula I.

Compounds of formula I are prepared as per the following flow chart.

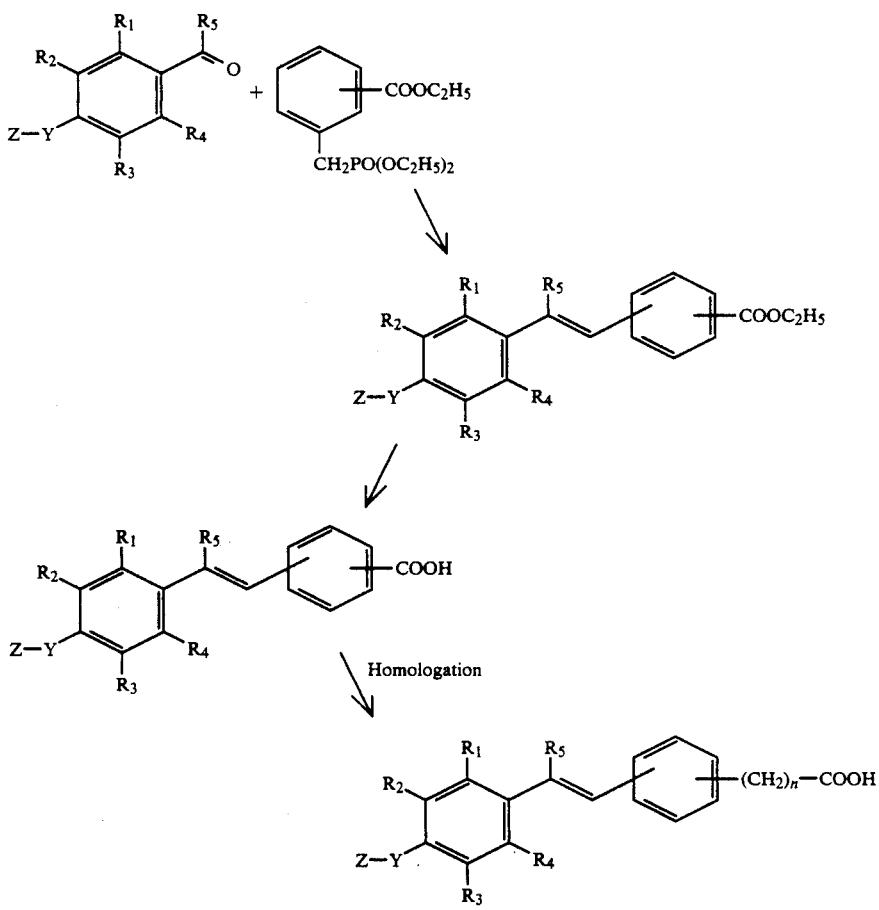

These acids may be converted to the salts, esters and amides. Also the acids may be converted to alcohols which can then be converted to aldehydes and ketones which can then be converted to corresponding acetals and ketals.

According to the above procedure, a diethyl (4-carboethoxybenzyl)phosphonate is reacted with a 4-alkoxy (or alkylthio) benzaldehyde or a 4-alkoxy (or alkylthio)-phenyl lower alkyl ketone in the presence of sodium hydride to give the ethyl benzoate compound of this invention.

Hydrolysis of the ester group by standard procedures gives the corresponding acid (formula V). The hydrolysis may be accomplished by basic saponification with an alkali metal base. For example, an ester of formula IV may be dissolved in a polar solvent such as an alkanol, preferably under an inert atmosphere at room temperature with about a three molar excess of base, for example, potassium hydroxide. The solution is stirred for an extended period of time, between 15 and 20 hours, cooled, acidified and the hydrolysate recovered by conventional means.

To prepare the compounds of formula VI where n is 1−5, the benzoic acid compounds of formula V are subjected to homologation by successive treatment using the Arndt-Eistert or similar procedure.

The pharmaceutically acceptable salts, esters and amides represented by formula I are obtainable from the acids of formula V.

Esterification is accomplished by refluxing the acid in a solution of the appropriate alcohol in the presence of thionyl chloride or by reacting the acid and the appropriate alcohol in the presence of 1,3-dicyclohexylcarbodiimide and 4-dimethylaminopyridine. The ester is recovered and purified by conventional means.

Salts are prepared by reacting the acid with an appropriate base by standard procedures.

The amide may be formed by any appropriate amidation means known in the art. One way to prepare such compounds is to first make an acid chloride and then treat that compound with ammonium hydroxide or an appropriate amine. For example, the acid is treated with an alcoholic solution of base such as ethanolic KOH (in approximately a 10% molar excess) and reacted at room temperature for about ½ hour. The solvent is removed and the residue taken up in an organic solvent such as ether, treated with a dialkyl formamide and then a 10-fold excess of oxalyl chloride. This is all effected at a reduced temperature between about −10° C. and +10° C. The last mentioned solution is then stirred at the reduced temperature for 1-4 hours, preferably 2 hours. Solvent removal provides a residue which is taken up in an inert organic solvent such as benzene, cooled to about 0° C. and treated with concentrated ammonium hydroxide. The resulting mixture is stirred at a reduced temperature for 1-4 hours. The product is recovered by conventional means.

Alcohols are made by converting the corresponding acids to the acid chloride as described above and then reducing the acid chloride with sodium borohydride (March, Ibid, pg. 1124), which gives the corresponding alcohols. Alkylating these alcohols with appropriate alkyl halides under Williamson reaction conditions (March, Ibid, pg. 357) gives the corresponding ethers.

Aldehydes can be prepared from the corresponding primary alcohols using mild oxidizing agents such as exemplified by pyridinium dichromate in methylene chloride (Corey, E. J., Schmidt, G., *Tet. Lett.*, 399, 1979).

Acetals can be prepared from the corresponding aldehyde by the method described in March, Ibid, p. 810.

The following examples are set out to illustrate the invention, not to limit its scope.

EXAMPLE 1

4-Carboethoxy-benzylbromide

To a stirred solution of 16.09 g (78 mmol) of 1,3-dicyclohexylcarbodiimide (Aldrich) in 100 ml methylene chloride was added a suspension of 15.4 g (71 mmol) of 4-carboxybenzylbromide in 100 ml methylene chloride and then 4.9 g (106.5 mmol) of absolute ethanol and 0.81 g (7.1 mmol) of 4-dimethylaminopyridine. A further 50 ml of methylene chloride was added to the reaction mixture and mixture heated at reflux for 2 h. The mixture was allowed to cool to room temperature and the resultant white precipitate removed by filtration. The filtrate was washed with water, dried (MgSO$_4$) and then concentrated in-vacuo to give the title compound as a colorless oil which crystallized on standing. PMR (CDCl$_3$): δ 1.39 (3H, t, J~7.2 Hz), 4.38 (2H, q, J~7.2 Hz), 4.50 (2H, s), 7.45 (2H, d, J~7.7 Hz), 8.03 (2H, d, J~7.7 Hz).

EXAMPLE 2

Diethyl (4-carboethoxybenzyl)phosphonate

A mixture of 11.8 g (48 mmol) of 4-carboethoxybenzylbromide and 12.0 g (72 mmol) of freshly distilled triethylphosphite was placed in a flask fitted with an argon inlet and a dry-ice cooled trap. A continuous stream of argon was passed over the stirred reaction mixture and mixture heated at 120~° C. for 3 hours at which time no further ethyl bromide was being formed. The residue was purified by vacuum distillation to give the title compound as a colorless oil, BP=170° C./0.35 mm). PMR (CDCl$_3$): δ 1.23 (6H, t, J~7.1 Hz), 1.39 (3H, t, J~6.9 Hz), 3.21 (2H, d, J~22.1 Hz), 4.02 (4H, m), 4.37 (2H, q, J ~7.5 Hz), 7.38 (2H, d, J~7.9 Hz), 8.00 (2H, d, J~7.9 Hz).

EXAMPLE 3

4-(3-Methyl-2-butenoxy)-acetophenone

A mixture of 7.5 g (55.1 mmol) of 4-hydroxyacetophenone, 7.6 g (55.1 mmol) of potassium carbonate and 150 ml of acetone was heated at reflux under argon for 1.5 hours. This mixture was then cooled in an ice-bath and treated slowly with a solution of 8.7 g (58.4 mmol) of 4-bromo-2-methyl-2-butene in 5 ml of acetone. The cooling bath was removed and mixture heated at reflux for 17 hours. The reaction mixture was cooled to room temperature and the solvent removed in-vacuo. The residue was treated with 100 ml water and extracted with 2×100 ml of ether. The ether extracts were combined and washed successively with 2×50 ml of 10% NaOH, 50 ml of water and 75 ml of saturated NaCl and then dried (MgSO$_4$). Solvent was removed in-vacuo and residue purified by Kugelrohr distillation (100° C., 0.25 mm) to give the title compound as a white solid.

PMR (CDCl$_3$): δ 1.76 (3H, s), 1.81 (3H, s), 2.53 (3H, s), 4.58 (2H, d, J~7.0 Hz), 5.50 (1H, t, J~7.0 Hz), 6.94 (2H, d, J~8.0 Hz), 7.92 (2H, d, J~8.0 Hz).

EXAMPLE 4

Ethyl 4-[E-2-methyl-2-[4-(3-methyl-2-butenoxy)-phenyl]ethenyl]benzoate and Ethyl 4-[Z-2-methyl-2-[4-(3-methyl-2-butenoxy)phenyl]ethenyl]benzoate 200 mg of 60% NaH in mineral oil (5 mmol) under argon was washed successively with three 2 ml portions of hexanes. 20 ml of the dry tetrahydrofuran (THF) and 40 mg of 15-Crown-5 (Aldrich) were then added to the reaction vessel and mixture cooled to 0° C. The reaction mixture was then treated with a solution of 1.0247 g (5.0614 mmol) of 4-(3-methyl-2-butenoxy)-acetophenone and 1.508 g (5.0218 mmol) of diethyl(4-carboethoxybenzyl)-phosphonate in 10 ml dry THF. The cooling bath was removed and the reaction mixture stirred at room temperature for 60 hours. The mixture was then treated with 100 ml water and extracted with 3×75 ml ether. The ether extracts were combined and washed successively with 2×25 ml of 10% sodium bisulphite and 50 ml saturated NaCl and then dried (MgSO$_4$). Solvent was removed in-vacuo and the residual oil purified by flash chromatography (silica; 10% ethyl acetate in hexanes) to give a mixture of the E and Z isomers. The mixture of E/Z isomers was separated by high pressure liquid chromatography (Whatman Partisil 10 M-9; 3% ethyl acetate in hexanes) to give the E-isomer as a white solid and the Z-isomer as a pale yellow oil.

E: PMR (CDCl$_3$): δ 1.43 (3H, t, J~7.4 Hz), 1.79 (3H, s), 1.84 (3H, s), 2.30 (3H, s), 4.41 (2H, q, J~7.4 Hz), 4.56 (2H, d, J~6.6 Hz), 5.54 (1H, t, J~6.6 Hz), 6.82 (1H, s) 6.95 (2H, d, J~8.1 Hz), 7.43 (2H, d, J~8.1 Hz), 7.49 (2H, d, J~8.9 Hz), 8.07 (2H, d. J~8.9 Hz).

Z: PMR (CDCl$_3$): δ 1.37 (3H, t, J~7.2 Hz), 1.77 (3H, s), 1.83 (3H, s), 2.23 (3H, s), 4.34 (2H, q, J~7.2 Hz), 4.52 (2H, d, J~6.9 Hz), 5.53 (1H, t, J~6.9 Hz), 6,47 91H, s), 6.85 (2H, d, J~8.4 Hz), 7.05, (2H, d, J~7.7 Hz), 7.10 (2H, d, J~8.4 Hz), 7.81 (2H, d, J~7.7 Hz).

EXAMPLE 5

4-(3-Methyl-2-thiobutenyl)bromobenzene

A mixture of 12.8 g (67.7 mmol) of sodium hydroxide in 50 ml acetone was heated at reflux under argon for 2.5 hours. The refluxing mixture was then treated dropwise with a solution of 10.0 g (67.1 mmol) of 4-bromo-2-methyl-2-butene in 10 ml acetone and the mixture heated at reflux for a further 24 hours. The mixture was then cooled and solvent removed in-vacuo. The residue was treated with 50 ml water and extracted with 3×75 ml ether.

The ether extracts were combined and washed successively with 3×30 ml of 5% NaOH, 50 ml of water and 50 ml of saturated NaCl and then dried (MgSO$_4$). Solvent was then removed in-vacuo and the residual oil purified by Kugelrohr distillation (70° C., 0.1 mm) to give the title compound as a colorless oil.

PMR (CDCl$_3$): δ 1.58 (3H, s), 1.70 (3H, s), 3.5 (2H, d, J~8.3 Hz), 7.36 (2H, d, J~8.3 Hz).

EXAMPLE 6

4-(3-Methyl-2-thiobutenyl)-benzaldehyde

To a solution of 1.9517 g (7.5886 mmol) of 4-(3-methyl-2-thiobutenyl)-bromobenzene in 25 ml dry ether at −78° C. under argon, was added dropwise 9.0 ml of 1.7 M (15.3 mmol) tert-butyllithium in pentane. The reaction mixture was stirred at −78° C. for 3 hours and then treated dropwise with a solution of 885.7 mg (12.12 mmol) of dimethylformamide in 6 ml dry ether. The cooling bath was then removed and the mixture stirred at room temperature for 26 hours, then cooled to 0° C. and treated with 75 ml of saturated $NH_4Cl$. This mixture was then extracted with 3×75 ml ether. The ether extracts were combined and washed successively with saturated $NaHCO_3$ and saturated NaCl solutions and then dried ($MgSO_4$). The solvent was then removed in-vacuo and residue purified by flash chromatography (silica; 10% ethyl acetate in hexanes) followed by Kugelrohr distillation (90° C., 0.25 mm) to give the title compound as a colorless oil.

PMR ($CDCl_3$: δ 1.74 (3H, s), 1.76 (3H, s), 3.66 (2H, d, J~6.9 Hz), 5.33 (1H, t, J~6.9 Hz), 7.35 (2H, d, J~8.8 Hz), 7.76 (2H, d, J~8.8 Hz), 9.92 (1H, s).

EXAMPLE 7

Ethyl 4-(E-2-(4-(3-methyl-2-thiobutenyl)phenyl)-ethenyl) benzoate

One hundred sixty milligrams of 60% NaH in mineral oil (4 mmol) under argon was washed successively with three 2 ml portions of hexane. 15 ml of dry THF and 70 mg of 15-Crown-5 were then added to the reaction vessel and mixture cooled to 0° C. The reaction mixture was then treated with a solution of 773.3 mg (3.7483 mmol) of 4-(3-methyl-2-thiobutenyl)-benzaldehyde and 1.1282 g (3.757 mmol) of diethyl-(4-carboethoxybenzyl)-phosphonate in 10 ml of dry THF. The cooling bath was then removed and the reaction mixture stirred at room temperature for 2 hours. The mixture was then treated with 100 ml water and extracted with 3×75 ml ether. The ether extracts were combined and washed successively with 2×25 ml of 10% sodium bisulphite and 50 ml of saturated NaCl and then dried ($MgSO_4$). Solvent was removed in-vacuo and the residue purified by flash chromatography (silica; 10% ethyl acetate in hexanes) to give a mixture of the E and Z isomers of the title compound. A portion of this mixture was recrystallized from an ether/hexanes mixture to give pure E-isomer as a white crystalline solid.

PMR ($CDCl_3$): δ 1.45 (3H, t, J~7.1 Hz), 1.67 (3H, s), 1.77 (3H, s), 3.62 (2H, d, J~7.8 Hz), 4.41 (2H, q, J~7.1 Hz), 5.36 (1H, t, J~7.8 Hz), 7.12 (1H, d, J~16.5 Hz), 7.21 (1H, d, J~16.5 Hz), 7.35 (2H, d, J~8.2 Hz), 7.48 (2H, d, J~8.2 Hz), 7.58 (2H, d, J~8.1 Hz), 8.07 (2H, d, J~8.1 Hz).

EXAMPLE 8

By the procedure of Examples 1–4 using the appropriately 2, 3, 5 and/or 6-substituted 4-carboethoxybenzylbromide as starting materials, the following compounds (in the E and Z isomeric forms) may be made:
ethyl 2-chloro-4-(2-methyl-2-(4-(3-methyl-2-butenoxy) phenyl)ethenyl)benzoate,
ethyl 3,5-dimethyl-4-(2-methyl-2-(4-(3-methyl-2-butenoxy)phenyl)ethenyl)benzoate,
ethyl 3,5-dimethoxy-4-(2-methyl-2-(4-3-methyl-2-butenoxy)phenyl)ethenyl)benzoate,
ethyl 2,6-dichloro-4-(2-methyl-2-(4-3-methyl-2-butenoxy)phenyl)ethenyl)benzoate, or
ethyl 2,3,5,6-tetramethoxy-4-(2-methyl-2-(4-(3-methyl-2-butenoxy)phenyl)ethenyl)benzoate.

EXAMPLE 9

Proceeding by the process of Examples 1–4, using 2-carboethoxybenzylbromide and 3-carboethoxybenzylbromide in place of the corresponding 4-carboethoxy compound, the following products (in the E and Z isomeric forms) are obtained:
ethyl 2-(2-methyl-2-4(4-(3-methyl-2-butenoxy) phenyl)ethenyl)benzoate, and
ethyl 3-(2-methyl-2-(4-(3-methyl-2-butenoxy) phenyl)ethenyl) benzoate.

EXAMPLE 10

By the procedure of Example 1, reacting 4-hydroxyacetophenone with
methyl bromide,
butyl bromide,
decyl bromide, or
6-bromo-2-hexene
gives the following intermediates:
4-methoxyacetophenone
4-butoxyacetophenone
4-decyloxyacetophenone
4-(4-hexenoxy)acetophenone
which, when reacted with diethyl-(4-carboethoxybenzyl)-phosphonate by the procedure of Example 4, gives the following products as the E and Z isomers:
ethyl 4-(2-methyl-2-(4-methoxyphenyl)ethenyl) benzoate,
ethyl 4-(2-methyl-2-(4-butoxyphenyl)ethenyl) benzoate,
ethyl 4-(2-methyl-2-(4-decycloxyphenyl)-ethenyl)-benzoate, or
ethyl 4-(2-methyl-2-(4-(4-hexenyloxy)-phenyl)ethenyl)benzoate.

The E and Z isomers can be separated by conventional means as described in Example 4.

EXAMPLE 11

To a solution of 100 mg of ethyl 4-(E-2-methyl-2-(4-(3-methyl-2-butenoxy)phenyl)ethenyl)-benzoate in 3 ml of ethanol under argon is added dropwise a solution of 50 mg of potassium hydroxide in 3 ml of ethanol and 1 ml of water. The mixture is stirred at room temperature for 18 hours, cooled and acidified with 3N hydrochloric acid. The resulting precipitate is dissolved in ether, the ether solution washed with saturated aqueous sodium chloride and concentrated to give a solid which is recrystallized from aqueous methanol to give 4-(E-2-methyl-2-(4-(3-methyl-2-butenoxy) phenyl)ethenyl) benzoic acid.

EXAMPLE 12

A mixture of 50 mg of 4-(2-methyl-2-(-4-(3-methyl-2-butenoxy)phenyl)ethenyl)benzoic acid and ethanolic potassium hydroxide is stirred at room temperature for 0.5 hours and solvent is removed in-vacuo. The residue is dissolved in 5 ml ether, treated with 1 drop of dimethylformamide, cooled to 0°, then treated with 150 mg of oxalyl chloride. After stirring at 0° for 2 hours, the mixture is filtered, the residue is washed with ether and the combined organic solutions concentrated. The residue is dissolved in benzene, cooled to 0. and treated dropwise with 2 ml of concentrated aqueous ammonium hydroxide. The mixture is stirred at 0° for 2 hours, diluted with 30 ml water and extracted with ether. The ether extract is washed with saturated aqueous sodium chloride, dried over magnesium sulfate and concentrated in-vacuo to give 4-(2-methyl-2(4-(3-methyl-2-butenoxy)phenyl)ethenyl) benzamide.

Using methylamine in place of ammonium hydroxide, the product is N-methyl-4-(2-methyl-2-(4-(3-methyl-2-butenoxy)phenyl)ethenyl)benzamide.

EXAMPLE 13

4-(2-Methyl-2-(4-(3-methyl-2-butenoxy)phenyl)ethenyl)benzoic acid is converted to the corresponding benzoyl chloride by treating the potassium salt of the acid with oxalyl chloride as described in Example 12. The benzoyl chloride is reacted with diazomethane and the resulting diazoketone is decomposed using silver oxide catalyst in methanol to give methyl 4-(2-methyl-2-(4-(3-methyl-2-butenoxy)phenyl)ethenyl)phenylacetate.

By the procedure of Example 11, the methyl phenylacetate is hydrolyzed to give 4-(2-methyl-2-(4-(3-methyl-2-butenoxy)phenyl)ethenyl)-phenylacetic acid.

Using this phenylacetic acid in the above procedures gives methyl 4-(2-methyl-2-(4-(3-methyl-2-butenoxy)-phenyl)-ethenyl)3-phenylpropionate and the corresponding phenylpropionic acid.

Similarly, the following compounds are obtained:
methyl 4-(2-methyl-2-(4-(3-methyl-2-butenoxy) phenyl)ethenyl)-4-phenylbutanoate,
methyl 4-(2-methyl-2-(4-(3-methyl-2-butenoxy) phenyl)ethenyl)-5-phenylpentanoate, and
methyl 4-(2-methyl-2-(4-(3-methyl-2-butenoxy) phenyl)ethenyl)-6-phenylhexanoate.

Hydrolysis of these methyl esters gives the corresponding phenylbutanoic acid, phenylpentanoic acid and phenylhexanoic acid compounds.

EXAMPLE 14

Ethyl 4-(E-2-(4-(3-methyl-2-thiobutenyl)phenyl)-ethenyl)benzoate is hydrolyzed by the procedure of Example 11 to give 4-(E-2-(4-(3-methyl-2-thiobutenyl)-phenyl)ethenyl)benzoic acid.

This benzoic acid is converted to the corresponding benzoylchloride as described in Example 12 and the benzoylchloride is reduced with sodium borohydride by standard procedures (J. March, "*Advanced Organic Chemistry*", 2nd Edition, McGraw-Hill Book Company, pg. 1124) to give 4-(E-2-(4-(3-methyl-2-thiobutenyl)-phenyl)ethenyl)benzyl alcohol.

Reacting the benzyl alcohol with methyl chloride under Williamson reaction conditions (March, Ibid, pg. 357) gives methyl 4-(E-2-(4-(3-methyl-2-thiobutenyl)-phenyl)-ethenyl)benzyl ether.

Similarly, using 4-(E-2-methyl-2-(4-(3-methyl-2-butenoxy)-phenyl)ethenyl)benzoic acid in procedures described above the following are obtained:
4-(E-2-methyl-2-(4-(3-methyl-2-butenoxy)phenyl) ethenyl)benzyl alcohol, and
methyl 4-(E-2-methyl-2-(4-(3-methyl-2-butenoxy) phenyl)ethenyl) benzyl ether.

EXAMPLE 15

Treatment of the benzyl alcohol compounds prepared as in Example 14 with pyridinium dichromate in methylene chloride by standard procedures gives:

4-(E-2-(4-(3-methyl-2-thiobutenyl)-phenyl)ethenyl)-benzaldehyde, and
4-(E-methyl-2-(4-(3-methyl-2-butenoxy)phenyl) ethenyl)benzaldehyde.

EXAMPLE 16

The benzaldehyde compounds, prepared as in Example 15, in ethanol solution are treated with hydrogen chloride gas by standard procedures to give:
4-(E-2-(4-(3-methyl-2-thiobutenyl)-phenyl)ethenyl)-benzaldehyde, diethyl acetal, and
4(E-2-methyl-2-(4-(-methyl-2-butenoxy)phenyl) ethenyl)benzaldehyde, diethyl acetal.

Reaction of the benzaldehyde compounds with ethylene glycol using an acid catalyst gives the corresponding cyclic ethylene acetals.

EXAMPLE 17

Preferably, these compounds may be administered topically using various formulations. Such formulation may be as follows:

| Ingredient | Weight/Percent |
|---|---|
| Solution | |
| Retinoid | 0.1 |
| BHT | 0.1 |
| Alcohol USP | 58.0 |
| Polyethylene Glycol 400 NF | 41.8 |
| Gel | |
| Retinoid | 0.1 |
| BHT | 0.1 |
| Alcohol USP | 97.8 |
| Hydroxypropyl Cellulose | 2.0 |

What is claimed is:

1. A compound of the formula

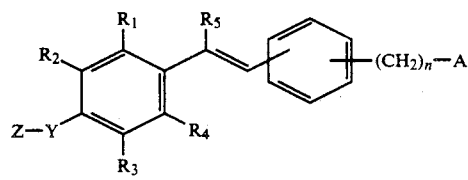

in which:
$R_1$, $R_2$, $R_3$ and $R_4$ are hydrogen, lower alkyl, halogen or lower alkoxy;
$R_5$ is hydrogen or lower alkyl;
Y is oxygen or sulfur;
Z is 1–10 carbon straight or branched alkyl, or 2–10 carbon straight or branched chain alkenyl or alkynyl;
n is 0–5; and
A is COOH, COOR$_7$, CONHR$_7$, CON(R$_7$)$_2$, —CH$_2$OH, —CH$_2$OR$_7$, CH$_2$OCOR$_7$, —CHO, CH(OR$_8$)$_2$, CHOR$_9$O, —COR$_6$ or CR$_6$(OR$_8$)$_2$, or CR$_6$OR$_9$O where R$_6$ is —(CH$_2$)$_m$CH$_3$ where m is 0–4, R$_7$ is alkyl of 1 to 10 carbons or aryl or alkylaryl group, R$_8$ is lower alkyl, and R$_9$ is divalent alkyl radical of 2 to 5 carbons, or a pharmaceutically acceptable salt of said compound.

2. A compound of claim 1 where Y is O.

3. A compound of claim 2 where n is 0, 1 or 2.

4. A compound of claim 3 where A is COOH, COOR$_7$, CONHR$_7$, or CON(R$_7$)$_2$.

5. A compound of claim 4 in which $R_1$, $R_2$, $R_3$ and $R_4$ are hydrogen.

6. A compound of claim 4 in which $R_1$, $R_2$, $R_3$ and $R_4$ are hydrogen and $R_5$ is methyl.

7. A compound of claim 4 in which Z-Y- is 3-methyl-2-butenoxy.

8. A compound of claim 1 where Y is S.

9. A compound of claim 8 where n is 0, 1 or 2.

10. A compound of claim 9 where A is COOH, $COOR_7$, $COONHR_7$, or $COON(R_7)_2$.

11. A compound of claim 10 in which $R_1$, $R_2$, $R_3$ and $R_4$ are hydrogen.

12. A compound of claim 10 in which $R_1$, $R_2$, $R_3$ and $R_4$ are hydrogen and $R_5$ is methyl.

13. A compound of claim 10 in which Z-Y- is 3-methyl-2-thiobutenyl.

14. A pharmaceutical composition having retinoid like activity, comprising a pharmaceutically acceptable excipient and an effective amount of a compound of claim 1.

15. A compound of claim 7 where A is COOH or $COOR_7$, n is 0, $R_1$, $R_2$, $R_3$ and $R_4$ are hydrogen, and the phenyl ring bearing the A group is para substituted.

16. A compound of claim 15 where $R_5$ is methyl.

17. The compound which is 4-(E-2-methyl-2-(4-(3-methyl-2-butenoxy)phenyl)ethenyl benzoic acid.

18. The compound which is ethyl 4-(E-2-methyl-2-(4-(3-methyl-2-butenoxy)phenyl)ethenyl benzoate.

19. A compound of claim 13 where A is COOH or $COOR_7$, n is 0, $R_1$, $R_2$, $R_3$ and $R_4$ are hydrogen, and the phenyl ring bearing the A group is para substituted.

20. A compound of claim 19 where $R_5$ is hydrogen.

21. The compound which is 4-(E-2-(4-(3-methyl-2-thiobutenyl)phenyl)ethenyl benzoic acid.

22. The compound which is ethyl 4-(E-2-(4-(3-methyl-2-thiobutenyl)phenyl)ethenyl benzoate.

* * * * *

UNITED STATES PATENT AND TRADEMARK OFFICE
CERTIFICATE OF CORRECTION

PATENT NO. : 4,992,468
DATED : February 12, 1991
INVENTOR(S) : Roshantha A.S. Chandraratna It is certified that error appears in the above-identified patent and that said Letters Patent is hereby corrected as shown below:

Column 2, line 46, "alkyphenyl" should be --alkylphenyl--;
Column 8, line 45, before "91H" insert --(--; and
Column 9, line 23, after "(CDCl$_3$" insert --)-- before the ":".

Signed and Sealed this

Fourteenth Day of December, 1993

Attest:

BRUCE LEHMAN

Attesting Officer

Commissioner of Patents and Trademarks